United States Patent [19]

Bouillon et al.

[11] 4,421,739

[45] Dec. 20, 1983

[54] BENZYLIDENE-CAMPHORS, PROCESSES FOR THEIR PREPARATION AND COSMETIC COMPOSITIONS CONTAINING THEM

[75] Inventors: Claude Bouillon, Eaubonne; Charles Vayssié, Aulnay-sous-Bois, both of France

[73] Assignee: L'Oreal, Paris, France

[21] Appl. No.: 886,560

[22] Filed: Mar. 14, 1978

[30] Foreign Application Priority Data

Mar. 15, 1977 [FR] France ............................... 77 07720
Sep. 9, 1977 [FR] France ............................... 77 27343

[51] Int. Cl.³ .................... C07C 49/433; A61K 7/42; C07C 49/627
[52] U.S. Cl. ........................................ 424/47; 560/19; 564/282; 560/51; 560/254; 564/285; 562/427; 562/433; 564/428; 562/462; 544/399; 544/159; 544/158; 544/162; 544/163; 544/175; 544/171; 546/284; 568/659; 568/808; 568/632; 568/634; 260/398; 204/158 R; 424/59; 568/327; 568/42; 260/453 RY; 260/457; 260/508; 260/509; 260/510; 260/511; 260/465 D; 260/465 E; 260/465 F; 260/501.12; 260/501.15; 560/9
[58] Field of Search ............ 260/590 B, 453 RY, 457, 260/508, 509, 510, 511, 465 D, 465 E, 465 F, 260/501.12, 501.15, 398; 424/59, 47; 568/327, 568/42; 560/9, 19, 51, 254; 562/427, 433, 462; 564/282, 285, 428; 544/399, 159, 158, 162, 163, 175, 544/171; 540/284; 568/659, 808, 532, 634; 204/158 R

[56] References Cited

U.S. PATENT DOCUMENTS 3,415,875 12/1968 Luethi et al. ........................ 424/59
3,449,732 7/1973 Rody et al. ........................ 424/59
3,781,417 12/1973 Welters et al. ..................... 424/59
3,821,307 6/1974 Hoch ................................ 260/590 B

FOREIGN PATENT DOCUMENTS 2407733 8/1974 Fed. Rep. of Germany ... 260/590 B
2282426 3/1976 France ........................... 260/590 B Primary Examiner—James H. Reamer
Attorney, Agent, or Firm—Fleit, Jacobson, Cohn & Price

[57] ABSTRACT

The invention provides compounds which are particularly valuable for use as the active ingredient in sun tan lotions and creams and the like. These compounds have the general formula:

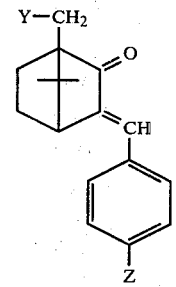

in which Y denotes hydrogen or the radical $SO_3H$ or a salt thereof with an organic or inorganic base, and Z denotes the radical $-CH_2Br$ or $-CHBrBr$ or a radical $Z'$ which denotes the radical $-CH_2I$, $-CH_2R$, $-CHR'R'$, $-CHO$ or $-COOR''$, in which R denotes $-NR_1R_2$, $-N^+R_1R_2R_3$, $-OR_4$, $-OCOR_5$, $-SR_6$, $-CN$, $-COOR''$ or $-SSO_3Na$, in which $R_1$ and $R_2$ independently denote hydrogen, $C_{1-18}$ alkyl or hydroxyalkyl, or $R_1$ and $R_2$, together with the nitrogen atom to which they are attached, denote a heterocyclic ring, $R_3$ denotes $C_{1-4}$ alkyl or hydroxyalkyl or sulphonatopropyl, $R_4$ denotes hydrogen, alkyl, polyoxyethylene, aryl which is optionally substituted, menthyl or dialkylaminoalkyl, $R_5$ denotes alkyl, alkenyl, aryl or a 5 or 6 membered heterocyclic ring which is optionally aromatic, and $R_6$ denotes hydrogen, alkyl, carboxyalkyl, aminoalkyl, hydroxyalkyl, aryl or 3-alanyl, $R'$ denotes $-OR'_4$ or $-SR'_6$, in which $R'_4$ and $R'_6$ are as defined under $R_4$ and $R_6$, respectively, except for hydrogen, polyoxyethylene, hydroxyalkyl, 3-alanyl and aryl, and $R''$ denotes hydrogen or alkyl, such that when R denotes $N^+R_1R_2R_3$, $R_1$ and $R_2$ are not hydrogen and either $R_3$ denotes sulphonatopropyl, or the compound is in the form of a salt with an anion, which is $SO_4$alkyl, $SO_3$aryl, $SO_3$alkyl or halogen or an inorganic or organic acid addition salt thereof when R denotes $-NR_1R_2$.

51 Claims, No Drawings

BENZYLIDENE-CAMPHORS, PROCESSES FOR THEIR PREPARATION AND COSMETIC COMPOSITIONS CONTAINING THEM

The present invention relates to p-monobromomethyl- and p-dibromomethyl-benzylidene-camphors, as well as to the process for their preparation and to their use in the field of cosmetics. The invention also relates to derivatives prepared from the abovementioned bromine-containing compounds, and to their use in the field of cosmetics.

The compounds of this invention have remarkable properties regarding absorption of actinic radiation of certain wavelengths and a very wide solubility range, and they can be used, in particular, in the preparation of cosmetic compositions intended for protecting the human epidermis.

It is known that light radiations of between 280 and 400 nanometers (nm) make it possible to tan the human epidermis, but that the zone between 280 and 320 nm causes erythema and skin burns, the seriousness of which increases rapidly with the exposure time. Thus, a good protective agent must have a high absorbing power in the zone from about 280 to 320 nm, but it must allow the radiation in the zone above 320 nm to pass through as much as possible, in order to offer the best conditions for bronzing without erythema. In addition, it must possess good photochemical, heat and chemical stability properties, especially in contact with perspiration, and good solubility in the various solvents and ingredients forming the vehicle of the cosmetic composition.

French Pat. No. 73/34,140 describes benzylidene-camphor derivatives carrying a quaternary ammonium radical on the benzene nucleus in the para-position relative to the bornylidene radical. French Pat. No. 74/05,427 describes benzylidene-camphor derivatives which are sulphonated on the methyl radical in the α-position to the carbonyl radical or on the benzene nucleus.

Although these compounds have good anti-actinic properties and can be used in cosmetic compositions for tanning the human epidermis, they are rather restricted in number. As a result, they do not give complete satisfaction, especially as regards the preparation of a wide range of formulations, in which they are not always compatible, especially for reasons of solubility or of compatibility with the solvents and ingredients which are usually employed in cosmetics.

This invention aims, in particular, to overcome the abovementioned disadvantages and to enable a vast family of compounds which, whilst each compound possesses good sunlight-filter properties, exhibits, with the various solvents and ingredients used in cosmetic compositions for bronzing the human epidermis, very selective protection as well as a wide range of solubilities and good compatibility, in particular when the composition comprises several phases.

The present invention provides the bromine-containing derivatives of para-methylbenzylidene-camphor which have the formula:

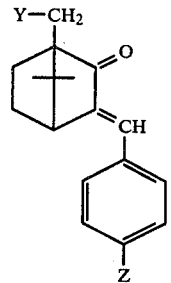

in which Y denotes H or the radical $SO_3H$ and its salts with organic or inorganic bases, and Z denotes the radical $-CH_2Br$ or $-CHBr_2$.

Amongst the compounds of the formula I, there may be mentioned the compounds of Table 1 below, in which table the number of each compound is the same as that of its preparation example.

TABLE 1

| No. of the compound | Name of the compound |
|---|---|
| 1 | 3-(4-bromomethylbenzylidene)-camphor |
| 2 | 3-(4-dibromomethylbenzylidene)-camphor |
| 52 | 3-(4-bromomethylbenzylidene)-camphor-10-sulphonic acid ($C_{18}H_{21}BrO_4S$); melting point = 232° C. as well as the salts of the above acid No. 52. |

The compounds of the formula I can be used either as synthesis intermediates for preparing the compounds of the formula II below, or as protective filters in cosmetic composition for protecting the human epidermis against actinic radiation.

The present invention thus also provides the compounds of the general formula II:

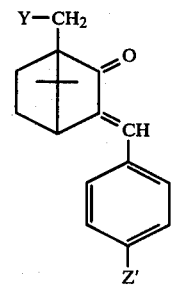

in which Y denotes H or $SO_3H$ and the corresponding salts with organic or inorganic bases, and Z' denotes the groups $-CH_2I$, $-CH_2R$, $-CHR'R'$, $-CHO$ or $-COOR''$, where $R = -NR_1R_2$, $-N^+R_1R_2R_3$, $-OR_4$, $-OCOR_5$, $-SR_6$, $-CN$, $-COOR''$ or $-S-SO_3Na$, in which $R_1$ and $R_2 = H$, $C_{1-18}$ alkyl or hydroxyalkyl, or they form, together with the nitrogen atom, a heterocyclic ring such as morpholine, piperidine, pyrrolidine, piperazine, N-methylpiperazine or N-phenylpiperazine, $R_3 = C_{1-4}$ lower alkyl, hydroxyalkyl or sulphonatopropyl, $R_4 = H$, alkyl, polyoxyethylene, aryl which may or may not be substituted, menthyl or dialkylaminoalkyl, $R_5 = $ alkyl, alkenyl, aryl, or a heterocyclic ring which may or may not be aromatic and contains 5 to 6 chain members, and $R_6 = H$, alkyl, carboxyalkyl, aminoalkyl, hydroxyalkyl, aryl or 3-alanyl, $R' = -OR'_4$ or $-SR'_6$, in which $R'_4$ and $R'_6$ can have respectively the same meanings as $R_4$ and $R_6$, except for the meanings hydrogen, polyoxyethylene, hydroxyalkyl, 3-alanyl and aryl, and R″=hydrogen or alkyl, it being understood that, when R=NR₁R₂, the compound can be in the form of an addition salt with an inorganic or organic acid, and that when R=N⁺R₁R₂R₃, where R₁ and R₂ are different from H, the molecule is ionically balanced either by R₃, when the latter has the meaning sulphonatopropyl, or by an anion X⁻, it being possible for X to have the meanings SO₄alkyl, SO₃aryl, SO₃alkyl or halogen.

The compounds of formula II can be used especially as protective filters in cosmetic compositions for protecting the human epidermis against actinic radiation.

Amongst the compounds of the invention, there may be mentioned, in particular, the compounds of Table 2 below, in which table the number of each compound is the same as that of its preparation example.

TABLE 2

| No. of the compound | Name of the compound |
|---|---|
| 3 | 3-(4-dimethylaminomethylbenzylidene)-camphor |
| 4 | 3-(4-diethylaminomethylbenzylidene)-camphor |
| 5 | 3-(4-diethylaminomethylbenzylidene)-camphor hydrochloride |
| 6 | 4-[(2-oxo-3-bornylidene)-methyl]-benzyldiethylammonium camphor-sulphonate |
| 7 | 3-[4-bis-(2-hydroxyethyl)-aminomethylbenzylidene]-camphor |
| 7 bis | 3-[4-bis-(2-hydroxyethyl)-aminomethylbenzylidene]-camphor hydrochloride |
| 8 | 3-(4-diisopropylaminomethylbenzylidene)-camphor |
| 8 bis | 3-(4-diisopropylaminomethylbenzylidene)-camphor hydrochloride |
| 9 | 3-(4-dibutylaminomethylbenzylidene)-camphor |
| 9 bis | 3-(4-dibutylaminomethylbenzylidene)-camphor hydrochloride |
| 10 | 3-[4-bis-(octadecyl)-aminomethylbenzylidene]-camphor |
| 11 | 3-(4-piperidinomethylbenzylidene)-camphor |
| 12 | 3-(4-morpholinomethylbenzylidene)-camphor |
| 13 | 4-[(2-oxo-3-bornylidenemethyl)-benzylamino]-benzoic acid |
| 14 | 4-(2-oxo-3-bornylidenemethyl)-benzyldiethylmethylammonium p-toluenesulphonate |
| 15 | 4-(2-oxo-3-bornylidenemethyl)-benzyldiethylmethylammonium methanesulphonate |
| 16 | N—[4-(2-oxo-3-bornylidenemethyl)-benzyl]-N—methyl-morpholinium methanesulphonate |
| 17 | N—[4-(2-oxo-3-bornylidenemethyl)-benzyl]-N—methyl-morpholinium methyl-sulphate |
| 18 | N—[4-(2-oxo-3-bornylidenemethyl)-benzyl]-N—methyl-morpholinium iodide |
| 19 | N—[4-(2-oxo-3-bornylidenemethyl)-benzyl]-N—methyl-piperidinium p-toluenesulphonate |
| 20 | N—[4-(2-oxo-3-bornylidenemethyl)-benzyl]-N—methyl-piperidinium methanesulphonate |
| 21 | 4-(2-oxo-3-bornylidenemethyl)-benzyltriethylammonium bromide |
| 22 | 4-(2-oxo-3-bornylidenemethyl)-benzyl-tris-(2-hydroxyethyl)-ammonium bromide |
| 23 | 4-(2-oxo-3-bornylidenemethyl)-benzyldimethyldodecyl-ammonium bromide |
| 24 | 4-(2-oxo-3-bornylidenemethyl)-benzyldimethyltetradecylammonium bromide |
| 25 | 3-(4-hydroxymethylbenzylidene)-camphor |
| 26 | 3-(4-methoxymethylbenzylidene)-camphor |
| 27 | 3-(4-butoxymethylbenzylidene)-camphor |
| 28 | 3-(4-dodecyloxymethylbenzylidene)-camphor |
| 29 | 3-(4-tetradecyloxymethylbenzylidene)-camphor |
| 30 | 3-(4-hexadecyloxymethylbenzylidene)-camphor |
| 31 | 3-(4-phenoxymethylbenzylidene)-camphor |
| 32 | 3-(4-α-naphthyloxymethylbenzylidene)-camphor |
| 33 | 3-(4-p-benzoylphenoxymethylbenzylidene)-camphor |
| 34 | methyl 2-[4-(2-oxo-3-bornylidenemethyl)-benzyloxy]-benzoate |
| 35 | 2-[4-(2-oxo-3-bornylidenemethyl)-benzyloxy]-benzoic acid |

TABLE 2-continued

| No. of the compound | Name of the compound |
|---|---|
| 36 | 4-(2-oxo-3-bornylidenemethyl)-benzyl tetradecanoate |
| 37 | 4-(2-oxo-3-bornylidenemethyl)-benzyl hexadecanoate |
| 38 | 4-(2-oxo-3-bornylidenemethyl)-benzyl benzoate |
| 39 | 3-(4-mercaptomethylbenzylidene)-camphor |
| 40 | 3-(4-methylthiomethylbenzylidene)-camphor |
| 41 | 3-(4-methylsulphinylmethylbenzylidene)-camphor |
| 42 | 2-[4-(2-oxo-3-bornylidenemethyl)-benzylthio]-acetic acid |
| 43 | 2-[4-(2-oxo-3-bornylidenemethyl)-benzylthio]-succinic acid |
| 44 | 3-[4-(2-oxo-3-bornylidenemethyl)-benzylthio]-alanine |
| 45 | 3-(4-β-diethylaminoethylthiomethylbenzylidene)-camphor hydrobromide |
| 46 | 3-[4-(benzothiazol-2-ylthiomethyl)-benzylidene]-camphor |
| 47 | 3-(4-cyanomethylbenzylidene)-camphor |
| 48 | 4-(2-oxo-3-bornylidenemethyl)-phenylacetic acid |
| 49 | 4-(2-oxo-3-bornylidenemethyl)-benzoic acid |
| 50 | 3-(4-dimethoxymethylbenzylidene)-camphor |
| 51 | 3-(4-formylbenzylidene)-camphor |
| 55 | 2-[4-(2-oxo-3-bornylidenemethyl)-benzylthio]-benzoic acid |
| 56 | 4-(2-oxo-3-bornylidenemethyl)-benzyl 2,5-dihydroxybenzoate |
| 57 | 4-(2-oxo-3-bornylidenemethyl)-benzyl 3,5-di-(t-butyl)-4-hydroxybenzoate |
| 58 | 4-(2-oxo-3-bornylidenemethyl)-benzyl oleate |
| 59 | 3-[4-(2-ethylhexyloxymethyl)-benzylidene]-camphor |
| 60 | 3-(4-octyloxymethylbenzylidene)-camphor |
| 61 | 3-(4-hexyloxymethylbenzylidene)-camphor |
| 62 | 3-(4-methyloxymethylbenzylidene)-camphor |
| 63 | 3-[4-(2,6-di-(t-butyl)-4-methylphenoxymethyl)-benzylidene]-camphor |
| 64 | 3-(4-dimethylaminoethoxymethylbenzylidene)-camphor |
| 65 | 3-[4-(2-oxo-3-bornylidenemethyl)-benzylthio]-propionic acid |
| 66 | 4-(2-oxo-3-bornylidenemethyl)-benzyltrimethyl-ammonium methyl-sulphate |
| 67 | N—[4-(2-oxo-3-bornylidenemethyl)-benzyl]-N—(2-hydroxyethyl)-morpholinium chloride |
| 68 | N—(2-hydroxyethyl)-N—[4-(2-oxo-3-bornylidenemethyl)-benzyl]-dimethylammonium bromide |
| 69 | 3-[4-(2-oxo-3-bornylidenemethyl)-benzyldimethyl-)ammonio]-propanesulphonate |
| 70 | 3-(4-oleyloxymethylbenzylidene)-camphor |
| 71 | 3-(4-iodomethylbenzylidene)-camphor |
| 72 | 3-(4-β-hydroxyethoxymethylbenzylidene)-camphor |
| 73 | 4-(2-oxo-3-bornylidenemethyl)-benzyldithiodiacetic acid |
| 74 | 3,3′-[4-(2-oxo-3-bornylidenemethyl)-benzyldithio]-dipropionic acid |
| 75 | α,α′-[4-(2-oxo-3-bornylidenemethyl)-benzyldithio]-disuccinic acid |
| 76 | 3-[4-(7-hydroxy-2,5-dioxaheptyl)-benzylidene]-camphor |
| 77 | N,N′—bis-[4-(2-oxo-3-bornylidenemethyl)-benzyl]-piperazine |
| 78 | N—methyl-N—[4-(2-oxo-3-bornylidenemethyl)-benzyl]-piperazinium bromide |
| 79 | N—methyl-N,N′—bis-[4-(2-oxo-3-bornylidenemethyl)-benzyl]-piperazinium bromide |
| 80 | N,N′—bis-(2-hydroxyethyl)-N,N′—bis-[4-(2-oxo-3-bornylidenemethyl)-benzyl]-piperazinium dibromide |
| 81 | N,N′—bis-(2-hydroxypropyl)-N,N′—bis-[4-(2-oxo-3-bornylidenemethyl)-benzyl]-piperazinium dibromide |
| 82 | N,N′—bis-(2-hydroxyethyl)-N—[4-(2-oxo-3-bornylidenemethyl)-benzyl]-piperazinium bromide |

The compounds of Table 2 can also exist in the form of addition salts with an inorganic or organic acid.

The compounds of formulae I and II exhibit an absorption maximum in the zone from 290 to 305 nm of the ultra-violet spectrum. They have the property of absorbing the major part of the so-called erythematogenic solar radiations, which are between 285 and 320 nm, and particularly of absorbing the most harmful radiations. For the absorption maximum, their molar absorption coefficient ($a_m$), calculated in acordance with French Standard Specification No. T 01-030, is very high, since it is greater than or equal to 25,000 on average, which corresponds to an exceptional absorbing power.

Whereas the coefficient ($a_m$) of known compounds has a maximum of the order of 24,500, the coefficient ($a_m$) of the compounds of the invention can reach 45,000, as indicated in Table 3 below:

TABLE 3

| No. of the compound of Table 1 or 2 | Wavelength in (nm) | Absorption coefficient ($a_m$) |
|---|---|---|
| 1 | 299 | 28,650 |
| 11 | 296 | 28,300 |
| 13 | 299 | 38,100 |
| 33 | 295 | 45,000 |
| 41 | 298 | 28,800 |
| 46 | 301 | 39,600 |
| 49 | 301 | 32,700 |
| 51 | 305 | 30,000 |
| A | 290 | 21,000 |
| B | 284 | 24,500 |

In this table, A is benzylidene-camphor, and 4-(2-oxo-3-bornylidenemethyl)-phenyl-trimethylammonium methyl-sulphate B, which respectively have the formulae:

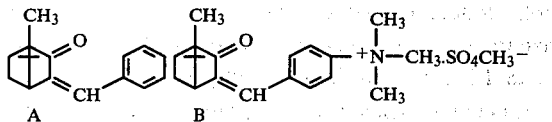

The excellent properties of absorption of the erythematogenic radiations, that is to say the radiations at between 285 and 320 nm, are shown for the compounds of the invention in Table 4 below, which indicates the percentage of transmitted radiations as a function of their wavelength. These values were determined by placing a 10 mm thickness of a solution, in 100 ml of ethanol, containing 2 mg of the compound to be examined, in the path of the incident radiation, and by calculating the ratio, expressed as a percentage, of the transmitted flux to the incident flux for various wavelengths of between 260 and 360 nm.

TABLE 4

| Wavelength of the incident flux in nm | Percentage of transmitted flux relative to the incident flux for the compounds below | | | | | | |
|---|---|---|---|---|---|---|---|
| | A | B | no. 1 | no. 11 | no. 13 | no. 33 | no. 46 | no. 49 |
| 260 | 29 | 26 | 51 | 49 | 25 | 22 | 25 | 35 |
| 270 | 10 | 12 | 23 | 20 | 8 | 10 | 10 | 15 |
| 280 | 3 | 7 | 8 | 7 | 3 | 3 | 4 | 4 |
| 290 | 2 | 8 | 3 | 3 | 1.5 | 1 | 2 | 1 |
| 300 | 3 | 18 | 2 | 2 | 1 | 1 | 1 | 0.5 |
| 310 | 11 | 58 | 4 | 5 | 2 | 5 | 3 | 1 |
| 320 | 55 | 94 | 15 | 21 | 9 | 33 | 12 | 4 |
| 330 | 86 | 98 | 63 | 69 | 43 | 76 | 50 | 38 |
| 340 | 90 | 100 | 91 | 91 | 74 | 89 | 86 | 72 |
| 350 | 92 | 100 | 95 | 96 | 86 | 93 | 95 | 82 |
| 360 | 92 | 100 | 95 | 98 | 91 | 98 | 98 | 86 |

In general terms, it is found that the protection provided by the compounds of the invention covers the range of so-called erythematogenic wavelengths more selectively than do compounds A and B, and that their absorbing power is greater than that of these compouns A and B.

The very large range of solubilities, offered by the compounds of the invention, in the usual cosmetic vehicles is shown by Table 5 below, in which the solubility of certain compounds is indicated in grams per 100 ml of solvent.

TABLE 5

| No. of the compound | Solvent | | |
|---|---|---|---|
| | water | ethanol | paraffin oil |
| 4 | 0 | 500 | 25 |
| 5 | 10 | 0.6 | 0 |
| 6 | 190 | 210 | 0 |
| 9 | 0 | 100 | 300 |
| 16 | 50 | 100 | 0 |
| 27 | 0 | 100 | 100 |
| 28 | 0 | 100 | 0 |
| 42 | 0 | 150 | 0 |

Thus, certain compounds have a solubility greater than 100% in water, ethanol or paraffin oil, whereas others are insoluble in the abovementioned solvents and, lastly, others are only soluble in one of the abovementioned solvents and insoluble in the other two.

The invention also provides a process for the preparation of the mono- and di-brominated compounds of the formula I. We have discovered that it is possible to obtain the abovementioned compounds by selectively brominating the compounds of the formula I':

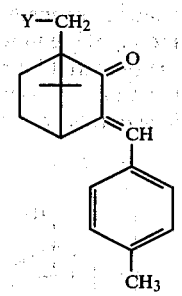

in which Y has the abovementioned meanings, in excellent yield with brominating the methyl radical situated in the α-position to the carbonyl radical of the camphor, or the double bond of the benzylidene, or the aromatic nucleus.

The bromination is suitably carried out either with bromine, or with N-bromosuccinimide, in an inert solvent, in the cold or with heating, and with exposure to radiation in the wavelength range from 200 to 800 nm, optionally in the presence of a neutralising agent.

When carried out in the cold, that is to say at ambient temperature, the reaction generally takes 3 to 4 hours; and when carried out under the action of heat, preferably under reflux, the reaction generally takes 30 to 60 minutes. Preferably chlorohydrocarbons such as carbon tetrachloride, or ether, acetic acid, benzene or carbon disulphide, are used as the inert solvents, and an alkali metal or alkaline earth metal carbonate is used as the neutralising agent.

In order to obtain the monobrominated compound of the formula I, in which Z denotes —$CH_2Br$, a rigorously stoichiometric amount of the reactants is used and the yield is virtually quantitative. At the end of the reaction, the inorganic salts which may have been formed can be filtered off, the solvents driven off, the residual mixture concentrated and a crude product obtained on cooling, which can be recrystallised, from a solvent such as isopropanol, with a yield of 85 to 90%. The mono- and di-brominated compounds of the formula I which are thus obtained can be stored easily without deterioration, without any special precautions being taken.

When the bromination is carried out with bromine, a solution of the latter in an inert solvent is introduced gradually, and whilst stirring, into a solution of the compound of the formula I in the same inert solvent. When the bromination is carried out with N-bromosuccinimide, all the reactants can be introduced into the inert solvent at the start of the operation, and the reaction is carried out whilst stirring, and preferably under the action of heat.

It is possible to first obtain the mono-brominated compound of the formula I, in which $Z = CH_2Br$, and to subsequently prepare the di-brominated compound of the formula I, in which $Z = CHBrBr$ from the mono-brominated compound, using either bromine or N-bromosuccinimide.

When it is desired to obtain a compound of the formula I in which Y denotes $SO_3H$, the reaction should be carried out in the absence of the neutralising agent, or the reaction is completed with an acidification.

The derivatives of the formula II can be prepared from the mono- and di-brominated compounds of the formula I.

In general terms, the compounds of the formula II which are mono-substituted on the methyl radical of the benzene nucleus, that is to say those in which $Z'$ has the meaning $-CH_2R$, can be prepared by reacting a compound of the formula I with a nucleophilic compound carrying the radical R in accordance with the equation:

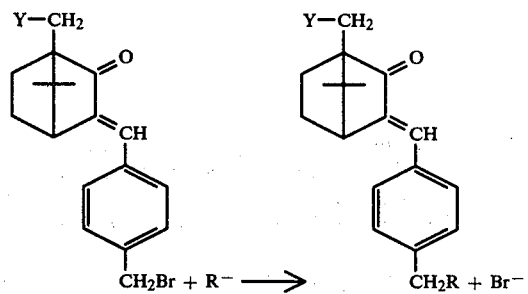

in which Y and R have the abovementioned meanings.

The amino compounds of the formula II, in which the radical R represents $-NR_1R_2$, can be prepared by reacting a compound of the formula, in which $Z = -CH_2Br$, with an excess of ammonia or of the corresponding amine of the formula $HNR_1R_2$, in an inert solvent, preferably a chlorine-containing solvent, an aromatic solvent, an alcohol, or also a dipolar aprotic solvent such as dimethylformamide, and optionally in the presence of a neutralising agent such as an alkali metal or alkaline earth metal carbonate. Amongst the amines which can be used, the following may be mentioned: dimethylamine, diethylamine, diisopropylamine, dibutylamine, distearylamine, diethanolamine, morpholine, piperidine, pyrrolidine, piperazine, N-methylpiperazine and N-phenylpiperazine.

This process is illustrated, in particular, by Examples Nos. 3,4,7,8,9 to 13 and 77 below.

The quaternary compounds of the formula II can be prepared by reacting a compound of the formula I, in which $Z = -CH_2Br$, with heat with a tertiary amine of the formula $NR_1R_2R_3$, in which the radicals $R_1R_2R_3$ each have the abovementioned meanings except hydrogen. The reaction can be carried out in the absence of solvents or in the presence of a solvent such as those already mentioned above.

This process is illustrated in Examples Nos. 21 to 24 and 78.

The compounds of the formula II, in which R represents $-OR_4$, $-SR_6$ and $-OCOR_5$, can be prepared by reacting either an alcohol or a phenol of the formula $HOR_4$, or a thiol of the formula $HSR_6$, or an acid of the formula $HO-COR_5$, respectively, with a mono-brominated compound of the formula I, the radicals $R_4$, $R_5$ and $R_6$ having the abovementioned meanings. In general, the reaction is carried out in the presence of an inorganic base, an alkali metal or alkaline earth metal hydroxide or carbonate, an alkali metal alcoholate, sodium hydride, an alkali metal, or also an organic base such as triethylamine.

In the above process, there may be mentioned:

The following alcohols and phenols: methanol, butanol, dodecanol, tetradecanol, hexadecanol, phenol, naphthol, hydroxybenzophenone, methyl salicylate, methyl 2-hydroxybenzoate, 2-ethylhexanol, oleyl alcohol, octanol, hexanol, dimethylaminoethanol, ethylene glycol, diethylene glycol, di-(t-butyl)-p-cresol and menthol;

the following thiols: methanethiol, thioglycolic acid, mercaptosuccinic acid, cysteine, diethylaminoethanethiol, 2-mercaptobenzothiazole, 2-mercaptobenzoic acid, 3-mercaptopropionic acid and $\beta$-aminoethanethiol; and the following acids: tetradecanoic, hexadecanoic, benzoic, gentisic, 3,5-di-(t-butyl)-4-hydroxybenzoic and oleic acids.

When $R_4$ represents hydrogen, the radical R then represents $-OH$, and a generator of OH ions, which can be a carbonate or a hydroxide as illustrated in Example 25, is used as the reactant.

Similarly, when $R_6$ represents hydrogen, either an alkali metal hydrosulphide or thiourea can be used as the reactant, and an alkaline hydrolysis is then carried out in accordance with the usual techniques for the preparation of thiols.

This process is illustrated, in particular, by Examples Nos. 39, 25, 36, 37, 38, 40, 42, 43, 44, 45, 46, 55, 26, 27, 28, 29, 30, 31, 32, 33, 34, 56, 57, and 60, and by those of Table 11.

The compounds of the formula II, in which $Z'$ represents $-CHR'R'$, the radical $R'$ represents $-OR'_4$ and the radical $R'_4$ having the abovementioned meanings, can be prepared in accordance with the equation:

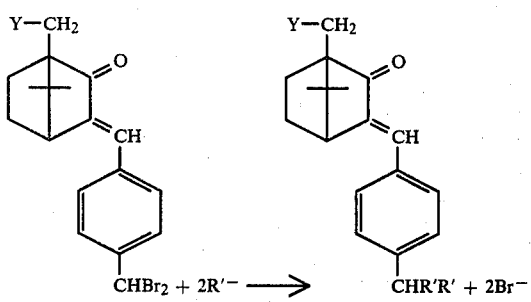

CHBr$_2$ + 2R'$^-$ $\longrightarrow$ CHR'R' + 2Br$^-$ in which Y and R' have the abovementioned meanings, by reacting a compound of the formula I, in which Z=CHBr$_2$, with an alcohol of the formula HOR'$_4$. The reaction is suitably carried out in the presence of a base, as in the process for the preparation of the monosubstituted compounds of the formula II which contain the radicals R$_4$ and R$_6$.

The use of methanol, as illustrated by Example 50, may be mentioned in the above process.

The aldehydes corresponding to the general formula II, in which Z' represents —CHO, can be prepared in accordance with the equation:

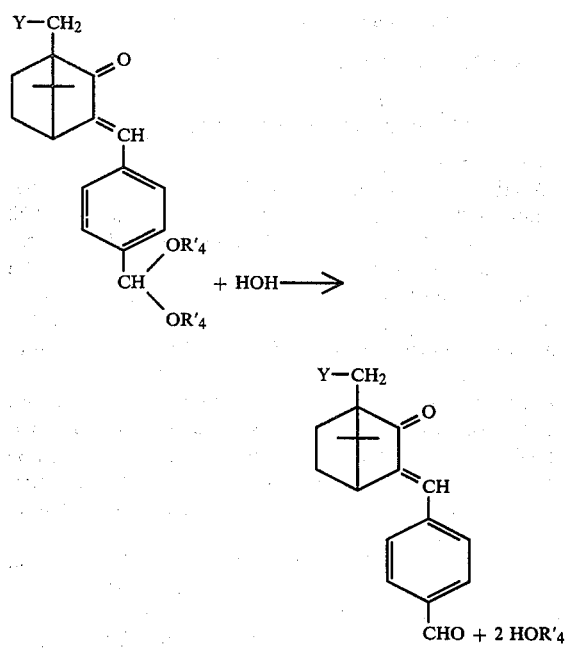

CHO + 2 HOR'$_4$ in which Y and R'$_4$ have the abovementioned meanings, by hydrolysing, in an acid aqueous medium, an acetal of the general formula II in which R' represents —OR'$_4$, as illustrated by Example 51.

Furthermore, the same aldehyde can be obtained by the direct oxidation of the monobrominated derivative of the formula I.

The compounds in which Z' represents —CHR'R', and R' represents SR'$_6$, are preferably prepared from the corresponding aldehyde, in which Z'=CHO, and from a thiol R'$_6$SH (2 molar equivalents) by acid catalysis in accordance with the known methods for the preparation of mercaptals; such a preparation is illustrated by Example 73.

The acids of the general formula II can be prepared in accordance with the equation:

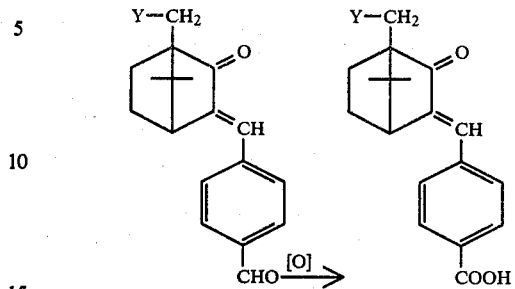

CHO $\xrightarrow{[O]}$ COOH in which Y has the abovementioned meanings, by oxidising an aldehyde of the general formula II, in which Z' has the meaning —CHO, as illustrated by Example 49.

The esters of the general formula II, in which Z' represents —COOR'', can be obtained by esterifying the acid by means of an alcohol of the formula HOR'' in which R'' has the abovementioned meanings.

The acids of the formula II, in which Z' represents —CH$_2$—COOH, can also be prepared by oxidising the corresponding nitriles of the formula II, which are themselves prepared by reacting a compound of the formula I with a cyanide, and the corresponding esters are obtained by esterifying by means of an alcohol of the formula HOR''. The compounds in which Z'=—CH$_2$I or CH$_2$S$_2$O$_3$Na can be obtained from a monobromo compound of formula I by reaction with respectively for example sodium iodide or with sodium thiosulphate, for example in an aqueous alcoholic medium or dimethylformamide, at 50 to 100 degrees C. Finally, the quaternary compounds of the general formula II can also be prepared by quaternising the compounds of the general formula Ii, in which Z' represents —CH$_2$-NR$_1$R$_2$ and in which R$_1$ and R$_2$ do not represent hydrogen. Amongst the quaternising agents which can advantageously be used, there may be mentioned: dimethyl and diethyl sulphates, alkyl halides or sulphonates, hydroxyalkyl halides and propanesultone, as illustrated, in particular, in Examples 14 to 20 and 66 to 69.

Finally, the present invention provides a cosmetic composition containing one or more compounds of the formula I or II together with a carrier or diluent, which compounds are stable to light radiation and which make it possible to provide an effective protection of the human epidermis (skin) against radiation in the range of erythematogenic wavelengths from 280 to 320 nm, but which selectively allow radiation having a wavelength greater than 320 nm to pass through, thereby providing excellent conditions for bronzing without erythema.

The composition of the invention can be in the form of, for example, a solution, a lotion, an emulsion such as a cream, a gel or a milk, or an oil, and in general in all the usual forms of anti-actinic cosmetic compositions. It can also contain cosmetic adjuvants such as thickeners, softening agents, superfatting agents, emollients, wetting agents and surface-active agents, as well as preservatives, anti-foam agents, perfumes or any other compatible ingredient usually employed in cosmetics. The composition can also contain one or more propellants, such as Freons, volatile hydrocarbons, carbon dioxide gas or nitrous oxide, and it can be in the form of a "spray" or an aerosol.

The composition of the invention generally contains 0.5 to 10%, and preferably 1.5 to 6%, by weight of one or more compounds of the formula I or Ii. Among suitable solvents used, there may be mentioned water, mono- or poly-alcohols containing 1 to 4 carbon atoms, as well as mixtures thereof and, aqueous-alcoholic solutions. The alcohols which are preferably used are ethanol, isopropyl alcohol, propylene glycol, glycerol, sorbitol and oleyl alchol, and the aqueous-alcoholic mixtures are preferably mixtures of water and ethyl alcohol.

The composition of the invention can be either colourless or coloured with colorants and/or pigments which are usually employed in anti-sunburn compositions, and especially with iron oxides, typically in an amount from 0.01 to 0.2% by weight relative to the total weight of the composition, as illustrated in Examples $B_4$, $B_5$ and $B_6$.

The very great flexibility of formulation offered by the use of the compounds of the formulae I and II is particularly apparent in compositions comprising different phases, such as "water-in-oil" or "oil-in-water" emulsions. In fact, as shown by Table 5, it is possible, in particular, to incorporate both a water-soluble compound and oil-soluble compound into the composition, in such a way that each of the phases contains an effective filter for stopping undesirable actinic radiation, by choosing from amongst the compounds having the desired solubility those which possess the best compatibility with the solvents and other ingredients contained in the composition. This great flexibility of formulation is made possible by means of the large number of the compounds of this invention, which, whilst exhibiting the same filtering properties, between the erythematogenic zone and the non-erythematogenic tanning zone (wavelength greater than 320 nm), offer a wide range of solubilities and compatibilities in relation to the usual cosmetic solvents and ingredients.

Amongst the examples of compositions containing a filter in each of the two phases, the compositions of Examples $A_7$, $B_1$ and $B_6$ may be especially mentioned.

The composition of the invention can also contain other agents which are known for their protective action against solar radiation, such as agents which absorb part of the radiation, like the abovementioned compounds A and B, as illustrated by Examples $A_1$ and $A_6$.

The composition of the invention can also contain agents which favour the hydration of the skin or slow down its dehydration, such as pyrrolidonecarboxylic acid salts, hydroxy-acid salts, amino-acids or urea, as illustrated in Example $B_8$, generally in an amount from 0.3 to 3% by weight.

When the composition contains amino compounds of the invention, it is advantageous, in order to obtain the desired solubility and compatibility characteristics, or to obtain the most favourable conditions of harmlessness, to use them in the form of a preparation which is prepared beforehand or at the time of use and which results from their total or partial neutralisation with an inorganic or organic acid. The composition then contains either the corresponding ammonium salt of the amino compound or a mixture of the abovementioned ammonium salt and the amino compound. Such a composition is illustrated by Examples $A_1$, $A_4$, $A_5$, $A_6$, $B_1$ and $B_7$.

Similarly, the composition can contain either acid compounds of the invention, or salts of these acids, or also mixtures resulting from their partial neutralisation with an inorganic or organic base, which neutralisation can be carried out beforehand or at the time of use, again in order to obtain advantageous conditions of solubility or compatibility, and/or better skin tolerance.

When the composition contains compounds of the invention which contain two different filtering activities, and especially in the case of compounds Nos. 13, 33, 34, 35 and 46, a particularly effective protection can be obtained.

The various types of composition of the invention are illustrated in the following manner: milks by Examples $A_1$ to $A_7$, creams by Examples $B_1$ to $B_8$, lotions by Examples $C_1$ to $C_5$, sprays by Examples $D_1$ to $D_4$, foams by Examples $E_1$ and $E_2$, and sun oils by Examples $F_1$ and $F_2$.

Amongst the cosmetic adjuvants included in the compositions of the invention in an amount of, say, 1 to 40% by weight relative to the weight of the composition, there may be mentioned lanolin, fatty acid triglycerides, glycerol, polyethylene glycols, oxyethyleneated lanolins, isopropyl palmitate and myristate, castor oil, cetyl/stearyl alcohol, glycerol monostearate, cetyl alcohol, butyl stearate and organic and inorganic waxes.

The Examples which follow, in which the percentages are by weight unless otherwise stated, and in which the temperatures are in degrees Centigrade, further illustrate the present invention.

PREPARATION EXAMPLES

EXAMPLE 1: Preparation of compound No. 1 of Table 1

3-(4-bromomethylbenzylidene)-camphor

1st method:

A mixture containing 127 g (0.5 mol) of p-tolylidene-camphor, 60 g of anhydrous sodium carbonate and 600 ml of carbon tetrachloride is heated under reflux. After complete homogenisation, the heating is stopped and a solution of 27.5 ml (0.5 mol) of bromine in 100 ml of carbon tetrachloride is then added, whilst exposing the reaction mixture to the action of a 150 watt lamp giving white light. The rate of introduction of the bromine is controlled so as to maintain a gentle reflux. At the end of the reaction, the inorganic salts which have formed are filtered off and the solution is concentrated to dryness. The residual solid is recrystallised from isopropanol and 144 g of pale yellow needles, which melt at 125°, are obtained.

Analysis: $C_{18}H_{21}BrO$: Calculated %: C 64.86; H 6.30; Br 24.02. Found %: C 64.90; H 6.42; Br 24.05.

2nd method:

A mixture containing 12.7 g (50 millimols) of p-tolylidene-camphor and 8.9 g (50 mmols) of N-bromosuccinimide in 100 ml of carbon tetrachloride is heated under reflux, whilst exposing it to the action of a 150 watt lamp giving white light. After filtration of the suspension thus obtained and concentration of the filtrate, 16.5 g of compound No. 1 are collected.

EXAMPLE 2: Preparation of compound No. 2 of Table 1

3-(4-dibromomethylbenzylidene)-camphor.

1st method:

A solution containing 203 g (0.8 mol) of p-tolylidene-camphor in 1,200 ml of carbon tetrachloride is heated to the boiling point with 195 g of anhydrous potassium carbonate, whilst stirring. 87.5 ml (1.6 mols) of bromine dissolved in 200 ml of carbon tetrachloride are introduced gradually, whilst exposing the whole to the action of a 150 watt lamp giving white light. The rate of introduction of the bromine and the heating are controlled so that the mixture is kept at the boiling point. At the end of the introduction, the heating is continued under illumination for about 30 minutes, the whole is then filtered and the filtrate is concentrated to dryness. The solid residue thus obtained is recrystallised from 600 ml of isopropanol. 278 g of compound No. 2 are collected in the form of pale yellow needles which melt at 96°.

Analysis: $C_{18}H_{20}BR_2O$: Calculated %: C 52.43; H 4.85; Br 38.83. Found %: C 52.42; H 4.99; Br 38.86.

2nd method:

50 mmols of N-bromosuccinimide and 50 mmols of 3-(4-bromomethylbenzylidene)-camphor in 100 ml of carbon tetrachloride are heated under reflux for 1 hour under illumination by a 150 watt lamp giving white light. The succinimide formed gradually comes together at the surface and it is filtered off. The filtrate is concentrated to dryness and 20.5 g of compound No. 2 are thus collected.

3rd method:

50 mmols of p-tolylidene-camphor and 100 mmols of N-bromosuccinimide are reacted under the operating conditions and solvent conditions indicated in the second method, but by heating under reflux for about 2 hours.

EXAMPLE 11: Preparation of compound No. 11 of Table 2

3-(4-piperidinomethylbenzylidene)-camphor.

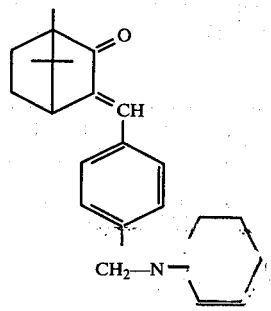

83 g of compound No. 1 are added, in portions using a spatula, to 100 ml of a solution containing 64 g of piperidine in ethanol. The mixture is stirred for 24 hours at ambient temperature, the whole is then filtered, the filtrate is concentrated, the residue is dissolved in a solution of sulphuric acid in ether and the resulting solution is filtered. The ether solution is concentrated to dryness to obtain 75 g of a residual solid which is recrystallised from a mixture of petroleum ether and isopropanol. Pale yellow crystals, which melt at 96°, are obtained.

Analysis: $C_{23}H_{31}NO$: Calculated %: C 81.90; H 9.20; N 4.15. Found %: C 81.80; H 9.00; N 4.05.

EXAMPLE 10: Preparation of compound No. 10 of Table 2

3-[4-bis-(octadecyl)-aminomethylbenzylidene]-camphor

A mixture containing 166.5 g of compound No. 1 and 521 g of distearylamine is stirred in a boiling water bath for 8 hours. After cooling, the whole is taken up with petroleum ether, the solution is filtered and the filtrate is concentrated to dryness. 290 g of a yellow product, which melts at 37°, are thus collected.

Analysis: $C_{54}H_{95}NO$: Calculated %: C 84.04; H 12.46; N 1.63. Found %: C 84.11; H 12.12; N 1.92.

EXAMPLE 4: Preparation of compound No. 4 of Table 2

3-(4-diethylaminomethylbenzylidene)-camphor

A solution containing 33 g of compound No. 1 and 22 g of diethylamine in 100 ml of carbon tetrachloride is heated at 60° for 30 minutes, whilst stirring. The precipitate is filtered off and the filtrate is concentrated to dryness. 31 g of a yellow oil, which is chromatographically pure, are obtained.

Analysis: $C_{22}H_{31}NO$: Calculated %: C 81.18; H 9.60; N 4.91. Found %: C 81.02; H 9.43; N 4.77.

The compounds Nos. 3, 7, 8, 9, 12, 13 and 77 of Table 2 are prepared by reacting an amine with 3-(4-bromomethylbenzylidene)-camphor in accordance with a method of operation which is analogous to that of Example 4, but using the corresponding amines for each compound, in the place of diethylamine, as indicated in Table 6 below. This table additionally mentions the solvent used, the temperature and the reaction time, as well as the melting point of the compound obtained or its appearance, and its calculated and found amine number, expressed in milliequivalents per gram.

TABLE 6

| Compound No. | Amine used, reacting with compound No. 1 | Solvent used | Reaction temperature | Reaction time | Melting point | Amine number milliequivalents/g Calculated | Found |
|---|---|---|---|---|---|---|---|
| 3 | dimethylamine | methanol | 20° | 120 hours | 65° | 3.37 | 3.41 |
| 7 | diethanolamine | ethanol | 80° | 5 hours | oil | 2.80 | 2.83 |
| 8 | diisopropylamine | ethanol | 80° | 6 hours | 89° | 2.83 | 2.85 |
| 9 | dibutylamine | ethanol | 80° | 2 hours | oil | 2.63 | 2.72 |
| 12 | morpholine | ethanol | 80° | 5 hours | 89° | 2.95 | 2.98 |
| 13 | piperazine p-amino-benzoate | methanol | 65° | 6 hours | 207° | 2.57 | 2.55 |
| 77 | piperazine p-amino-benzoate | ethanol | 80° | 1 hour | 204° | 2.39 | 2.39 |

Preparation of the salts formed with an inorganic or organic acid from the amino compounds of the formula II The acid is generally introduced, at ordinary temperature or with gentle heating, into a solution of the amino compound of the formula II. The mixture is concentrated to dryness and the residue is crystallised from an appropriate solvent. By way of examples, Table 7 below indicates the conditions of the preparation of the compounds Nos. 5, 6, 7 bis, 8 bis and 9 bis of Table 1 from the corresponding amino compounds, the acid and the solvent used being mentioned in each case. For each compound obtained, this table also indicates the crystallisation solvent, the melting point and the calculated and found percentage elementary analysis of C, H and N.

methyl ethyl ketone. 86 g of product are thus obtained in the form of whitish platelets melt at 155°.

Analysis: $C_{30}H_{41}NO_4S$:
Calculated %: C 70.41; H 8.08; N 2.74; S 6.27.
Found %: C 70.31; H 7.96; N 2.92; S 6.41.

TABLE 7

| Compound No. | Starting compound No. | Acid used | Solvent used | Melting point (crystallisation solvent) | C Calculated | C Found | H Calculated | H Found | N Calculated | N Found |
|---|---|---|---|---|---|---|---|---|---|---|
| 6 | 4 | camphor-sulphonic | ethanol | 170° (AcOEt) | 68.90 | 68.96 | 8.49 | 8.39 | 2.51 | 2.41 |
| 5 | 4 | hydro-chloric | acetone | 245° (iPrOH) | 73.00 | 72.97 | 8.91 | 8.88 | 3.87 | 4.08 |
| 7 bis | 7 | hydro-chloric | ethanol | 230° (iPrOH) | 67.09 | 67.22 | 8.13 | 8.19 | 3.56 | 3.57 |
| 8 bis | 8 | hydro-chloric | ether | 205° (iPrOH) | 73.91 | 74.13 | 9.30 | 9.12 | 3.59 | 3.34 |
| 9 bis | 9 | hydro-chloric | water | 139° (MIBK) | 74.70 | 74.70 | 9.64 | 9.47 | 3.35 | 3.42 |

MIBK = methyl isobutyl ketone;
AcOEt = ethyl acetate
iPrOH = isopropanol

PREPARATION OF THE QUATERNISED COMPOUNDS OF THE FORMULA II

EXAMPLE 14: Preparation of compound No.14 of Table 2

4-(2-oxo-3-bornylidene-methyl)-benzyldiethylmethylammonium p-toluenesulphonate 65 g of compound No. 4 of Table 2 and 41 g of methyl p-toluenesulphonate are heated under reflux in toluene for 4 hours 30 minutes. After cooling, the precipitate which has formed is drained and recrystallised from A method of operation which is analogous to that of Example 14 makes it possible to prepare compounds Nos. 15 to 24, 66 to 69 and 78 of Table 2, as indicated in Table 8 below. For each compound prepared, this table mentions the compound of the formula II or the starting amine, the quaternisation agent which can be monobrominated compound of the formula I, such as those included in Table 1, the solvent used and the reaction time. For each compound obtained, the table also indicates the melting point, as well as the calculated and found percentage elementary analysis of C, H and N.

TABLE 8

| Compound No. | Amine compound of the formula II or starting amine | Quaternisation agent | Solvent | Reaction time | Melting point | C Calculated | C Found | H Calculated | H Found | N Calculated | N Found |
|---|---|---|---|---|---|---|---|---|---|---|---|
| 15 | Compound No. 4 | $CH_3SO_3CH_3$ | (without solvent) | 30 minutes | 162° | 66.17 | 66.33 | 8.56 | 8.54 | 3.22 | 3.04 |
| 16 | Compound No. 12 | $CH_3SO_3CH_3$ | toluene | 5 hours | 192° | 64.14 | 64.30 | 7.80 | 7.72 | 3.12 | 3.04 |
| 17 | Compound No. 12 | $SO_4(CH_3)_2$ | ethyl acetate | 3 hours | 160° | 61.94 | 61.80 | 7.53 | 7.26 | 3.01 | 3.25 |
| 18 | Compound No. 12 | $ICH_3$ | $ICH_3$ | 4 hours | 200° | 57.38 | 57.24 | 6.65 | 6.85 | 2.91 | 2.73 |
| 19 | Compound No. 11 | $CH_3$ p-tolyl-$SO_3$ | toluene | 10 hours | 167° | 71.13 | 71.20 | 7.84 | 7.81 | 2.68 | 2.77 |
| 20 | Compound No. 11 | $CH_3SO_3CH_3$ | toluene | 5 hours | 170° | 67.11 | 67.37 | 8.28 | 8.20 | 3.13 | 3.08 |
| 21 | $N(C_2H_5)_3$ | Compound No. 1 | (without solvent) | 15 minutes | 230° | 63.71 | 63.56 | 8.40 | 8.18 | 3.10 | 2.70 |
| 23 | $C_{12}H_{25}N(CH_3)_2$ | Compound No. 1 | toluene | 4 hours | 83° | 70.31 | 70.35 | 9.59 | 9.29 | 2.56 | 2.41 |
| 24 | $C_{14}H_{29}N(CH_3)_2$ | Compound No. 1 | benzene | 5 hours | 100° | 71.08 | 71.30 | 9.76 | 9.55 | 2.44 | 2.52 |
| 66 | Compound No. 3 | $SO_4(CH_3)_2$ | ethyl acetate | 1 hour | 177° | 62.41 | 62.34 | 7.80 | 8.05 | 3.31 | 3.30 |
| 67 | Compound No. 12 | $ClCH_2CH_2OH$ | (without solvent) | 8 hours | 200° | 68.65 | 68.50 | 8.10 | 8.33 | 3.34 | 3.12 |
| 68 | Compound No. 3 | $BrCH_2CH_2OH$ | methyl ethyl ketone | 3 hours | 210° | 62.56 | 62.37 | 7.58 | 7.69 | 3.32 | 3.29 |
| 69 | Compound No. 3 | propane-sultone | toluene | 5 hours | 260° (hemi-hydrate) | 64.48 | 64.48 | 7.94 | 8.03 | 3.27 | 3.18 |
| 78 | N—methyl-piperazine | Compound No. 1 | toluene | 3 hours | 200° | 63.74 | 64.05 | 7.62 | 7.86 | 6.47 | 6.21 |
| 22 | $N(C_2H_4OH)_3$ | Compound No. 1 | (without solvent) | | oil | 59.75 | 59.51 | 7.47 | 7.55 | 2.90 | 2.92 |
| 82 | N,N'—bis-(hydroxyethyl)- | Compound No. 1 | toluene | 2 hours | 184° | 61.54 | 61.54 | 7.69 | 7.78 | 5.52 | 5.37 |

TABLE 8-continued

| Compound No. | Amine compound of the formula II or starting amine piperazine | Quaternisation agent | Solvent | Reaction time | Melting point | Elementary analysis | | | | | |
|---|---|---|---|---|---|---|---|---|---|---|---|
| | | | | | | C | | H | | N | |
| | | | | | | Calculated | Found | Calculated | Found | Calculated | Found |

EXAMPLE 25: Preparation of compound No. 25 of Table 2

3-(4-hydroxymethylbenzylidene)-camphor 33 g of compound No. 1 are added all at once to an ethanolic solution containing 6.2 g of potassium hydroxide, and the whole is heated to the boiling point. The mixture is kept under reflux for one hour and then evaporated to dryness. The residue is taken up with benzene and, after filtration, the benzene extract is concentrated to dryness. A pale yellow solid is thus obtained which, after crystallisation from petroleum ether, gives pale yellow crystals which melt at 35°.

Analysis: $C_{18}H_{22}O_2$:
Calculated %: C 80.00; H 8.15.
Found %: C 80.18; H 8.31.

EXAMPLE 27: Preparation of compound No. 27 of Table 2

3-(4-butoxybenzylidene)-camphor 19.5 g of sodium butylate are prepared by allowing 4.6 g of sodium to react with 50 ml of butanol. At the end of the reaction, 66.6 g of compound No. 1 and 100 ml of toluene are added. The mixture is heated in a boiling water-bath for 8 hours, it is then filtered and the filtrate is concentrated to dryness. 64 g of a pale yellow oil are thus collected, which can be distilled to give an oily product having a boiling point of 210° under a pressure of 0.5 mm Hg.

Analysis: $C_{22}H_{30}O_2$:
Calculated %: C 80.98; H 9.20.
Found %: C 80.66; H 9.07.

Compounds Nos. 26, 28 and 30 are prepared in accordance with a method of operation which is analogous to that of Example 27, except that the butanol is replaced by methanol (Example 26), dodecanol (Example 28) and hexadecanol (Example 30) respectively, and that, in Example 26, methanol is used as the solvent instead of toluene. The following compounds are obtained respectively:

Compound No. 26: melting point of 175° under a pressure of 0.25 mm Hg.
Analysis: $C_{18}H_{24}O_2$:
Calculated %: C 80.28; H 8.45.
Found %: C 80.29; H 8.46.

Compound No. 28: pale yellow oil which cannot be distilled.
Analysis: $C_{30}H_{46}O_2$:
Calculated %: C 82.19; H 10.50.
Found %: C 82.05; H 10.27.

Compound No. 30: pale yellow solid which melts at 40°.
Analysis: $C_{34}H_{54}O_2$:
Calculated %: C 82.59; H 10.93.
Found %: C 82.33; H 10.75.

EXAMPLE 29: Preparation of compound No. 29 of Table 2

3-(4-tetradecyloxymethylbenzylidene)-camphor 75 g of myristyl alcohol are introduced into a solution containing 18.9 g of sodium methylate in methanol. After the mixture obtained has been evaporated to dryness, the residue is taken up with benzene and 116.5 g of compound No. 1 are added. The mixture is heated under reflux for 8 hours, it is then filtered, the filtrate is evaporated to dryness and the oily residue obtained is distilled. 111 g of an oil (boiling point=250° under a pressure of 0.2 mm Hg) are thus collected, which solidifies rapidly to give a beige solid which melts at 35°.

Analysis: $C_{32}H_{50}O_2$:
Calculated %: C 82.40; H 10.73.
Found %: C 82.22; H 10.70.

EXAMPLE 31: Preparation of compound No. 31 of Table 2

3-(4-phenoxymethylbenzylidene)-camphor 11.6 g of sodium phenate are prepared by reacting the corresponding amounts of phenol and sodium hydroxide in an alcoholic solution, followed by evaporation to dryness. The phenate collected is stirred under reflux for 10 hours with 33.3 g of compound No. 1 in 100 ml of methyl ethyl ketone. After filtration of the reaction mixture, the filtrate is evaporated to dryness. 26 g of a white product, which melts at 139°, are obtained.

Analysis: $C_{24}H_{26}O_2$:
Calculated %: C 83.24; H 7.51.
Found %: C 83.27; H 7.62.

EXAMPLE 34: Preparation of compound No. 34 of Table 2 methyl 2-[4-(2-oxo-3-bornylidenemethyl)-benzyloxy]-benzoate.

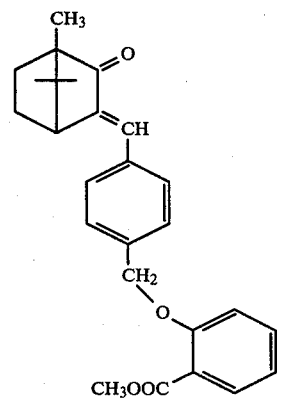

A methanolic solution containing 7.6 g (50 mmols) of methyl salicylate, 2 g of sodium hydroxide and 16.5 g (50 mmols) of compound No. 1 are heated at the boiling point for 4 hours. The reaction mixture is concentrated to dryness and the residue is extracted with hot benzene. The benzene solution is concentrated and the residue is crystallised from methanol. 14 g of white crystals, which melt at 120°, are thus obtained.

Analysis: $C_{26}H_{28}O_4$:
Calculated %: C 77.23; H 6.93.
Found %: C 77.07; H 7.06.

Compounds Nos. 32, 33, 36, 37 and 38 of Table 2 are prepared in an analogous manner to that of Example 34. For this purpose, compound No. 1 is used in each case, but the methyl salicylate is replaced by α-naphthol (Example 32), 4-hydroxybenzophenone (Example 33), myristic acid (Example 36), palmitic acid (Example 37) or benzoic acid (Example 38), respectively.

For each example, Table 9 below indicates the hydroxylic compound or acid which reacts with compound No. 1, the reaction time, the number of the compound obtained, its melting point and the corresponding calculated and found percentage elementary analysis of C and H.

PREPARATION OF THE THIOETHERS

EXAMPLE 39: Preparation of compound No. 39 of Table 2

3-(4-mercaptomethylbenzylidene)-camphor.

7.6 g (0.10 mol) of thiourea and 33 g (0.10 mol) of compound No. 1 are heated under reflux in isopropanol for 1 hour. The precipitate which has formed is filtered off and 35 g of the isothiouronium salt, which melts at 264°, are thus collected.

Analysis: $C_{10}H_{25}BrN_2OS$:
Calculated %: C 55.74; H 6.16; S 7.83.
Found %: C 55.74; H 6.37; S 7.83.

25 g of the isothiouronium salt are hydrolysed by prolonged heating with an excess of sodium hydroxide in an aqueousethanolic medium. After neutralisation with an acid, the product which has precipitated is drained and crystallised from methyl isobutyl ketone. White crystals, which melt at 87°, are obtained.

Analysis: $C_{18}H_{22}OS$:

TABLE 9

| Compound No. | Hydroxylic compound or acid, reacting with compound No. 1 | Reaction time | Melting point | Elementary analysis |  |  |  |
|---|---|---|---|---|---|---|---|
| | | | | C | | H | |
| | | | | Calculated % | Found % | Calculated % | Found % |
| 32 | α-naphthol | 6 hours | 120° | 84.85 | 84.62 | 7.07 | 7.38 |
| 33 | 4-hydroxy-benzophenone | 5 hours | 122° | 82.67 | 82.53 | 6.67 | 6.61 |
| 36 | myristic acid | 2 hours | 29° | 80.00 | 79.74 | 10.00 | 9.98 |
| 37 | palmitic acid | 6 hours | 30° | 80.31 | 80.58 | 10.24 | 10.27 |
| 38 | benzoic acid | 8 hours | 63° | 80.21 | 80.28 | 6.95 | 6.99 |

EXAMPLE 35: Preparation of compound No. 35 of Table 2

2-[4-(2-oxo-3-bornylidenemethyl)-benzyloxy]-benzoic acid.

Compound 34 is heated under reflux in an alcoholic solution of potassium hydroxide for 3 hours. The acid is precipitated by acidification, and a white product, which melts at 128°, is obtained.

Analysis: $C_{25}H_{26}O_4$:
Calculated %: C 76.92; H 6.67.
Found %: C 77.01; H 6.96.

Calculated %: C 75.48; H 7.74; S 11.19.
Found %: C 75.49; H 7.61; S 11.10.

The thioethers of the formula II are prepared in an analogous manner to that of Example 39 by heating compound No. 1 and the corresponding thiol compound at a moderate temperature in the presence of a basic agent. This agent can be omitted if the thiol product itself contains a basic function, for example a tertiary amine function. The product is then separated off in accordance with the usual techniques.

The conditions for the preparation of compounds Nos. 40, 42 to 46 and 55 of Table 2 are indicated in Table 10 below.

For each compound prepared, this table mentions the thiol compound used in the place of the thiourea of Example 39, the base and the solvent used, the reaction temperature and reaction time, as well as the number of the compound obtained, its melting point and its calculated and found percentage elementary analysis of C, H and S.

TABLE 10

| Compound No. | Thiol compound reacting with compound No. 1 | Base | Solvent | Temperature | Reaction time | Melting point | Elementary analysis | | | | | |
|---|---|---|---|---|---|---|---|---|---|---|---|---|
| | | | | | | | C | | H | | S | |
| | | | | | | | Calculated % | Found % | Calculated % | Found % | Calculated % | Found % |
| 40* | $CH_3SH$ | $CH_3ONa$ | ethanol | 40° | 1 hour | 44° | 76.00 | 76.18 | 8.00 | 8.05 | 10.67 | 10.87 |
| 42 | $HO_2C-CH_2-SH$ | NaOH | (mixture: water/methanol) | 60° | 1 hour 30 minutes | 90° | 69.73 | 69.79 | 7.02 | 7.02 | 9.31 | 9.45 |

TABLE 10-continued

| Compound No. | Thiol compound reacting with compound No. 1 | Base | Solvent | Temperature | Reaction time | Melting point | C Calculated % | C Found % | H Calculated % | H Found % | S Calculated % | S Found % |
|---|---|---|---|---|---|---|---|---|---|---|---|---|
| 43 | thiomalic acid<br>HO₂C—CH—SH<br>        |<br>HO₂C—CH₂ | N(C₂H₅)₃ | acetone | 20° | 45 hours | 210° | 65.65 | 65.84 | 6.51 | 6.49 | 7.97 | 8.10 |
| 44 | cysteine | KOH | mixture: (water/ethanol) | 60° | 2 hours | 190° | 67.53 | 67.36 | 7.29 | 7.27 | 8.58 | 8.64 |
| 45 | (C₂H₅)₂N—CH₂—CH₂—SH | (no basic agent) | methanol | 65° | 1 hour | 169°** | 61.79 | 61.67 | 7.78 | 7.64 | 6.87 | 7.07 |
| 46 | 2-mercapto-benzothiazole | CO₃Na₂ | ethanol | 80° | 1 hour | 114° | 71.56 | 71.58 | 6.01 | 6.20 | 15.28 | 15.23 |
| 55 | thiosalicylic acid | N(C₂H₅)₃ | acetone | 20° | 2 hours | 198° | 73.89 | 73.68 | 6.40 | 6.57 | 7.88 | 7.83 |

*Compound No. 41, which, after recrystallisation from ethanol, is in the form of a white solid which melts at 119°, is obtained by oxidising compound No. 40 with hydrogen peroxide.

Analysis $C_{19}H_{24}O_2S$
   Calculated %    C 72.11    H 7.64    S 10.13
   Found %          72.08       7.72      10.37
**Melting point of the hydrobromide.

EXAMPLE 47: Preparation of compound No. 47 of Table 2

3-(4-cyanomethylbenzylidene)-camphor 7 g of compound No. 1 of Table 1 are added to a methanolic solution containing 2.5 g of potassium cyanide, and the whole is heated under reflux for 30 minutes. The mixture obtained is concentrated to dryness, the residue is taken up with water, and the insoluble fraction is filtered off and crystallised from ethanol to obtain whitish crystals which melt at 127°.
Analysis: $C_{19}H_{21}NO$:
Calculated %: C 81.68; H 7.58; N 5.01.
Found %: C 81.41; H 7.36; N 5.22.

EXAMPLE 48: Preparation of compound No. 48 of Table 2

4-(2-oxo-3-bornylidenemethyl)-phenylacetic acid.

0.050 mol of compound No. 47 of Table 2 is heated under prolonged reflux with an excess of a mixture of acetic acid and hydrochloric acid, and, after filtering and washing, white crystals are obtained which melt at 134°.
Analysis: $C_{19}H_{22}O_3$: acid number (milliequivalents/g):
Calculated 3.36; Found: 3.33.

EXAMPLE 50: Preparation of compound No. 50 of Table 2

3-(4-dimethoxymethylbenzylidene)-camphor 1 mol of compound No. 2 of Table 1 is heated under reflux for two hours in a methanolic solution containing 2 mols of sodium methylate. The mixture is concentrated to dryness, the residue is extracted with benzene, the extract is filtered and the filtrate is then evaporated to dryness. A pale yellow powder, which melts at 98°, is thus obtained.
Analysis: $C_{20}H_{26}O_3$:
Calculated %: C 76.43; H 8.28.
Found %: C 76.26; H 8.47.

EXAMPLE 51: Preparation of compound No. 51 of Table 2

3-(4-formylbenzylidene)-camphor

By completely hydrolysing compound No. 50 of Table 2 in a mixture of water and dioxane in the presence of hydrochloric acid, and after having concentrated the solvent, a pale yellow product, which melts at 116°, separates out.
Analysis: $C_{18}H_{20}O_2$:
Calculated %: C 80.60; H 7.46.
Found %: C 80.64; H 7.56.
The same compound No. 51 can also be prepared by completely oxidising compound No. 1 using dimethyl sulphoxide in the presence of potassium carbonate.

EXAMPLE 49: Preparation of compound No. 49 of Table 2

4-(2-oxo-3-bornylidenemethyl)-benzoic acid

Compound No. 51 of Table 2 is oxidised with potassium permanganate in a mixture of water and acetone. After filtering off the precipitate and washing it with the same mixture of water and acetone, a white product, which melts at 240°, is obtained by acidifying the filtrate.
Analysis: $C_{18}H_{20}O_3$:
Calculated %: C 76.06; H 7.04.
Found %: C 76.17; H 7.06.

EXAMPLE 56: Preparation of compound No. 56 of Table 2

4-(2-oxo-3-bornylidenemethyl)-benzyl 2,5-dihydroxybenzoate.

Compound 56 is prepared according to Example 31 from gentisic acid; it is a white powder which melts at 220°.
Analysis: $C_{25}H_{26}O_5$:
Calculated %: C 73.89; H 6.40.
Found %: C 73.82; H 6.57.

EXAMPLE 57: Preparation of compound No. 57 of Table 2

4-(2-oxo-3-bornylidenemethyl)-benzyl 3,5-di-(t-butyl)-4-hydroxybenzoate

Compound 57 is prepared according to Example 31 from 3,5-di-(t-butyl)-4-hydroxybenzoic acid, replacing methyl ethyl ketone with dimethylformamide. It is in the form of a pale yellow solid which melts at 132°.
Analysis: $C_{33}H_{42}O_4$:
Calculated %: C 78.88; H 8.37.
Found %: C 79.13; H 8.42.

EXAMPLE 60: Preparation of compound No. 60 of Table 2

3-(4-octyloxymethylbenzylidene)-camphor

A suspension of 2.1 g (50 millimols) of sodium hydride (in oil) is added in small amounts to 6.5 g (50 millimols) of octan-1-ol in 100 ml of toluene, whilst stirring. When the evolution of hydrogen has ended, 16.6 g (50 millimols) of 3-(p-bromomethylbenzylidene)-camphor are added in portions, and the mixture is then heated under reflux for 3 hours. After adding water, the toluene phase is decanted, dried and concentrated to dryness. The residual syrup is distilled under reduced pressure. 8.8 g of a yellow liquid, which boils at 240° under a pressure of 0.1 mm Hg, are thus collected.
Analysis: $C_{26}H_{38}O_2$:
Calculated %: C 81.67; H 9.95.
Found %: C 81.52; H 10.15.

The compounds of the following Table 11 are prepared under the same conditions:

adding water, filtered off and drained. 70 g of a yellow solid, which melts at 108°, are obtained.
Analysis: $C_{18}H_{21}IO$:
Calculated %: C 56.84; H 5.53; I 33.42.
Found %: C 56.58; H 5.60; I 33.18.

EXAMPLE 73: Preparation of compound No. 73 of Table 2

4-(2-oxo-3-bornylidenemethyl)-benzyldithiodiacetic acid

A solution of 26.8 g of compound 51 and 16.4 g of thioglycolic acid is heated at the boiling point in dichloroethane for 3 hours, in the presence of concentrated sulphuric acid. The mixture is then concentrated to dryness. The residue is extracted with ether; the ether phase is washed with water and then concentrated to dryness. 38 g of a whitish solid, which melts at 116°, are thus obtained.
Acid number: Calculated: 4.61 milliequivalents/g.
Found: 4.64 milliequivalents/g.

EXAMPLE 79: Preparation of compound No. 79 of Table 2

N-methyl-N,N'-bis-[4-(2-oxo-3-bornylidenemethyl)-benzyl]-piperazinium bromide 33 g of compound 1 and 5 g of N-methylpiperazine are stirred in toluene (200 ml) at ordinary temperature for 1 hour, in the presence of sodium carbonate (6 g). The insoluble material is filtered off, made into a slurry again with a mixture of water and toluene and then drained. After drying, 23 g of a white solid, which melts at about 200° with decomposition, are collected.

TABLE 11

| | | | | Elementary analysis | | | |
|---|---|---|---|---|---|---|---|
| | | | | C | | H | |
| Compound No. | Alcohol used | Reaction time | Melting or boiling point | Calculated % | Found % | Calculated % | Found % |
| 62 | menthol | 4 hours | oil | 82.35 | 82.16 | 9.80 | 9.88 |
| 59 | 2-ethylhexanol | | oil | 81.67 | 81.98 | 9.95 | 9.95 |
| 70 | oleyl alcohol | 8 hours | oil | 83.08 | 83.16 | 10.77 | 11.19 |
| 64 | dimethylaminoethanol | 3 hours | hydrochloride melting point = 152° | 69.91 | 69.70 | 8.53 | 8.66 |
| 72 | ethylene glycol | 5 hours | boiling point = 195° under a pressure of 0.3 mm Hg melting point 54° | 76.45 | 76.48 | 8.28 | 8.14 |
| 76 | diethylene glycol | 6 hours | oil | 73.74 | 73.77 | 8.38 | 8.25 |

EXAMPLE 63: Preparation of compound No. 63 of Table 2

3-[4-(2,6-di(t-butyl)-4-methylphenoxymethyl)-benzylidene]-camphor

Compound 63 is prepared according to Example 29 from di-(tertiary butyl)-p-cresol, replacing the benzene by dimethylformamide. A whitish powder, which melts at 135°, is obtained.
Analysis: $C_{33}H_{44}O_2$:
Calculated %: C 83.90; H 9.32.
Found %: C 83.94; H 9.52.

EXAMPLE 71: Preparation of compound No. 71 of Table 2

3-(4-iodomethylbenzylidene)-camphor

A mixture of 66.6 g of compound 1 and 40 g of sodium iodide in acetone (500 ml) is heated under reflux for three hours. The reaction product is precipitated by

| Determinations: | | |
|---|---|---|
| | Tertiary amine number | Ionised bromine |
| Calculated % | 1.46 milliequivalents/g | 1.46 milliequivalents/g |
| Found % | 1.48 milliequivalents/g | 1.47 milliequivalents/g |

COMPOSITION EXAMPLES

In general terms, the compounds of the formula I or II can be incorporated directly into a composition intended for protecting the human epidermis against solar radiation. However, when they are in the form of an acid, that is to say that at least one of the radicals Y and Z' denotes an acid radical, they can be easily neutralised to the preferred pH using an inorganic or organic base which is chosen depending on the desired cosmetic properties and on the desired solubility. Likewise, the basic amino compounds according to the invention can be neutralised to the preferred pH with an inorganic or organic acid.

A. COMPOSITIONS OF ANTI-SUNBURN MILKS

Example $A_1$

The medium-protection anti-sunburn milk indicated below is prepared:

| | |
|---|---|
| oxyethyleneated cetyl/stearyl alcohol containing 25 mols of ethylene oxide E.O., that is to say "containing 25 EO" | 5 |
| cetyl alcohol | 1 |
| 2-octyldodecanol | 15 |
| Codex vaseline oil | 5 |
| unsaponifiable constituents of lucerne | 0.2 |
| benzylidene-camphor | 1 |
| compound No. 6 | 2.5 |
| methyl para-hydroxybenzoate q.s. | |
| perfume | 0.5 |
| water   q.s.p. | 100 |

Example $A_2$

The following anti-sunburn milk is prepared:

| | |
|---|---|
| Sipol wax | 5 |
| vaseline oil | 6 |
| isopropyl myristate | 3 |
| silicone oil | 1 |
| cetyl alcohol | 1 |
| glycerol | 20 |
| preservative | 0.3 |
| perfume | 0.3 |
| compound No. 22 | 3 |
| water   q.s.p. | 100 |

Example $A_3$

The following non-ionic anti-sunburn protective milk is prepared:

| | |
|---|---|
| Sipol wax | 5 |
| vaseline oil | 6 |
| isopropyl myristate | 3 |
| dimethylpolysiloxane | 1 |
| cetyl alcohol | 1 |
| preservative | 0.3 |
| glycerol | 20 |
| compound No. 14 | 2.5 |
| perfume | 0.5 |
| water   q.s.p. | 100 |

Example $A_4$

The following anti-sunburn milk is prepared:

| | |
|---|---|
| Sipol wax | 5 |
| vaseline oil | 6 |
| isopropyl myristate | 3 |
| dimethylpolysiloxane | 1 |
| cetyl alcohol | 1 |
| preservative | 0.3 |
| glycerol | 20 |
| compound No. 7 | 3 |
| perfume | 0.5 |
| malic acid | 1.2 |
| water   q.s.p. | 100 |

Example $A_5$

The following protective milk is prepared:

The same composition as in Example A is prepared, except that compound No. 6 and benzylidene-camphor are replaced by:

| | |
|---|---|
| compound No. 42 | 0.5 |
| magnesium salt of compound No. 42 | 2.9 |

Example $A_6$

The following anti-sunburn milk is prepared:

| | |
|---|---|
| oxyethyleneated cetyl/stearyl alcohol containing 25 mols of ethylene oxide E.O., that is to say "containing 25 EO" | 5 |
| cetyl alcohol | 1 |
| 2-octyldodecanol | 15 |
| Codex vaseline oil | 5 |
| unsaponifiable constituents of lucerne | 0.2 |
| benzylidene-camphor | 1 |
| compound No. 42 neutralised to pH 6 with 5 N aqueous potassium hydroxide | 3 |
| methyl para-hydroxybenzoate   q.s. | |
| perfume | 0.5 |
| water   q.s.p. | 100 |

Example $A_7$

The following non-ionic anti-sunburn protective milk is prepared:

| | |
|---|---|
| Sipol wax | 5 |
| vaseline oil | 6 |
| isopropyl myristate | 3 |
| dimethylpolysiloxane | 1 |
| cetyl alcohol | 1 |
| preservative | 0.3 |
| glycerol | 20 |
| compound No. 6 | 2.5 |
| compound No. 9 | 2 |
| perfume | 0.5 |
| water   q.s.p. | 100 |

B. COMPOSITIONS OF ANTI-SUNBURN CREAMS:

Example $B_1$

The following high-protection anti-sunburn cream is prepared:

| | |
|---|---|
| poloxyethyleneated hydrogenated palm oil "containing 15 EO" | 5 |
| cetyl/stearyl alcohol "containing 15 EO" | 5 |
| lanolin | 3 |
| lanolin alcohols | 1 |
| sunflower oil | 5 |
| vaseline oil | 10 |
| compound No. 26 | 2.5 |
| compound No. 8 bis | 4 |
| propylene glycol | 5 |
| preservatives   q.s. | |
| perfume | 0.5 |
| water   q.s.p. | 100 |

Example $B_2$

The following anti-sunburn cream is prepared:

| | |
|---|---|
| cetyl/stearyl alcohol | 2 |
| glycerol monostearate | 4 |

| | |
|---|---|
| cetyl alcohol | 4 |
| vaseline oil | 5 |
| butyl stearate | 5 |
| propylene glycol | 7 |
| silicone oil | 0.125 |
| 0.5% strength polyox | 3.5 |
| preservative | 0.3 |
| perfume | 0.4 |
| compound No. 14 | 4 |
| water q.s.p. | 100 |

Example B$_3$

The following non-ionic anti-sunburn protective cream is prepared:

| | |
|---|---|
| Sipol wax | 7 |
| glycerol monostearate | 2 |
| vaseline oil | 15 |
| silicone oil | 1.5 |
| cetyl alcohol | 1.5 |
| preservative | 0.3 |
| glycerol | 10 |
| compound No. 27 | 5 |
| perfume | 0.5 |
| water q.s.p. | 100 |

Example B$_4$

The following anionic anti-sunburn protective cream is prepared:

| | |
|---|---|
| self-emulsifying glycerol monostearate | 6 |
| polyoxyethyleneated sorbitan monostearate "containing 60 EO" | 2 |
| stearic acid | 2 |
| cetyl alcohol | 1.2 |
| lanolin | 4 |
| vaseline oil | 30 |
| preservative | 0.3 |
| triethanolamine | 0.1 |
| compound No. 37 | 3 |
| iron oxides | 0.2 |
| perfume | 0.5 |
| water q.s.p. | 100 |

Example B$_5$

The following anti-sunburn cream is prepared:

| | |
|---|---|
| cetyl/stearyl alcohol | 2 |
| glycerol monostearate | 4 |
| cetyl alcohol | 4 |
| vaseline oil | 5 |
| butyl stearate | 5 |
| propylene glycol | 7 |
| silicone oil | 0.125 |
| 0.5% strength polyox | 3.5 |
| preservative | 0.3 |
| perfume | 0.4 |
| compound No. 49 | 1 |
| iron oxides | 0.01 |
| potassium hydroxide | 0.45 |
| water q.s.p. | 100 |

Example B$_6$

The following anionic protective cream is prepared:

| | |
|---|---|
| self-emulsifying glycerol monostearate | 6 |
| polyoxyethyleneated sorbitan monostearate "containing 60 EO" | 2 |
| stearic acid | 2 |
| cetyl alcohol | 1.2 |
| lanolin | 4 |
| vaseline oil | 30 |
| preservative | 0.3 |
| triethanolamine | 0.1 |
| compound No. 29 | 2 |
| compound No. 7 | 3 |
| iron oxides | 0.1 |
| perfume | 0.6 |
| water q.s.p. | 100 |

Example B$_7$

The following anit-sunburn cream, which is partially neutralised, is prepared:

| | |
|---|---|
| cetyl/stearyl alcohol | 2 |
| glycerol monostearate | 4 |
| cetyl alcohol | 4 |
| vaseline oil | 5 |
| butyl stearate | 5 |
| propylene glycol | 7 |
| silicone oil | 0.125 |
| 0.5% strength polyox | 3.5 |
| preservative | 0.3 |
| perfume | 0.4 |
| compound No. 52 | 0.75 |
| triethanolamine salt of compound No. 52 | 3 |

Example B$_8$

The following moisturising anti-sunburn cream is prepared:

| | |
|---|---|
| Sipol wax | 7 |
| glycerol monostearate | 2 |
| vaseline oil | 15 |
| silicone oil | 1.5 |
| cetyl alcohol | 1.5 |
| preservative | 0.3 |
| glycerol | 10 |
| compound No. 27 | 5 |
| sodium pyrrolidonecarboxylate | 2 |
| perfume | 0.5 |
| water q.s.p. | 100 |

An analogous good result is obtained by replacing the sodium pyrrolidonecarboxylate, in the above anti-sunburn cream, with sodium glycolate in an amount of 1 g, or by adding 1 g of sodium glycolate to the composition of Example B$_2$

C. EXAMPLES OF ANTI-SUNBURN LOTIONS

Example C$_1$

The following anti-sunburn lotion is prepared:

| | |
|---|---|
| lanolin | 2.5 |
| butyl hydroxyanisole | 0.025 |
| butyl hydroxytoluene | 0.025 |
| octyl gallate | 0.0125 |
| triglycerides of C$_8$–C$_{12}$ fatty acids | 40 |
| perfume | 1.25 |
| compound No. 28 | 4 |
| 96° strength alcohol q.s.p. | 100 |

Example C₂

The following anti-sunburn lotion is prepared:

| | |
|---|---|
| glycerol | 5 |
| polyethylene glycol 400 | 0.5 |
| oxyethyleneated lanolin | 1 |
| soluble perfume | 2 |
| compound No. 16 | 2 |
| 96° strength alcohol | 50 |
| water    q.s.p. | 100 |

Example C₃

The following aqueous-alcohlic anti-sunburn lotion is prepared:

| | |
|---|---|
| compound No. 14 | 3 |
| glycerol | 5 |
| polyethylene glycol 400 | 0.5 |
| 96° strength alcohol | 50 |
| soluble perfume | 2 |
| water    q.s.p. | 100 |

Example C₄

The following oily-alcoholic anti-sunburn lotion is prepared:

| | |
|---|---|
| compound No. 8 bis | 3 |
| triglycerides of C₈–C₁₂ fatty acids | 40 |
| 96° strength ethanol | 56.5 |
| perfume | 0.5 |

Example C₅

The following anti-sunburn lotion is prepared:

| | |
|---|---|
| compound No. 19 | 10 |
| glycerol | 5 |
| 96° strength alcohol | 50 |
| polyethylene glycol 400 | 0.5 |
| oxyethyleneated lanolin | 1 |
| soluble perfume | 2 |
| water    q.s.p. | 100 |

D. EXAMPLES OF ANTI-SUNBURN SPRAYS

Example D₁

The following anti-sunburn spray is prepared:

| | |
|---|---|
| absolute alcohol | 30 |
| isopropyl myristate | 20 |
| castor oil | 2 |
| lanolin | 5 |
| perfume | 1 |
| compound No. 17 | 2 |
| Freon 12 | 40 |

Example D₂

The following oily-alcoholic anti-sunburn spray is prepared:

| | |
|---|---|
| compound No. 27 | 3 |
| absolute alcohol | 30 |
| isopropyl myristate | 24 |
| castor oil | 2 |
| perfume | 1 |
| Freon 12 | 40 |

Example D₃

The following anti-sunburn spray is prepared:

| | |
|---|---|
| absolute alcohol | 35 |
| methylene chloride | 20 |
| compound No. 1 | 2.5 |
| isopropyl myristate | 20 |
| castor oil | 2 |
| lanolin | 5 |
| perfume | 1 |
| carbon dioxide gas q.s.p. to a pressure of 8 bars. | |

Example D₄

The following anti-sunburn spray is prepared:

| | |
|---|---|
| absolute alcohol | 30 |
| methylene chloride | 15 |
| compound No. 1 | 1 |
| benzylidene-camphor | 1.5 |
| isopropyl myristate | 20 |
| castor oil | 2 |
| perfume | 1 |
| nitrous oxide q.s.p. to a pressure of 8 bars. | |

E. EXAMPLES OF AEROSOL FOAMS

Example E₁

The following liquid mixture is initially prepared:

| | |
|---|---|
| Sipol wax | 3.5 |
| vaseline oil | 6 |
| isopropyl myristate | 3 |
| preservative | 0.3 |
| glycerol | 10 |
| perfume | 0.3 |
| compound No. 15 | 2.5 |
| water    q.s.p. | 100 |

Thereafter, the aerosol foam container is made up; it contains, in each case, in percentage by weight:

| | |
|---|---|
| above liquid mixture | 87 |
| Freon F 12 | 13 |

Example E₂

The following liquid mixture for an aerosol foam is prepared:

| | |
|---|---|
| cetyl/stearyl and oleyl/cetyl alcohols containing 25 E.O. (50:50 mixture) | 3.5 |
| vaseline oil | 6 |
| isopropyl myristate | 3 |
| preservative | 0.3 |
| glycerol | 10 |
| perfume | 0.3 |
| compound No. 37 | 2.5 |
| water | q.s.p. 100 |

The aerosol foam container is made up, it contains the following:

| | |
|---|---|
| above liquid mixture | 85 |
| nitrous oxide | 15 |

F. EXAMPLES OF SUN OILS

Example $F_1$

The following sun oil is prepared:

| | | |
|---|---|---|
| compound No. 29 | | 10 |
| ethanol | | 10 |
| perfume | | 0.6 |
| castor oil | q.s.p. | 100 |

Example $F_2$

The following sun oil is prepared:

| | | |
|---|---|---|
| compound No. 36 | | 2 |
| perfume | | 0.6 |
| ethanol | | 15 |
| propylene glycol | | 10 |
| isopropyl palmitate | q.s.p. | 100 |

In general, analogous good results are obtained when:

in compositions $A_1$ to $A_7$, the compound or compounds of the invention is or are replaced by at least one of compounds Nos. 6, 7, 9, 14, 22, 42, 8 bis, 27 and 37;

in compositions $B_1$ to $B_8$, the compound or compounds of the invention is or are replaced by at least one of compounds Nos. 8 bis, 26, 27, 29, 37, 49 and 52;

in compositions $C_1$ to $C_5$, the compound or compounds of the invention is or are replaced by at least one of compounds Nos. 8 bis, 14, 16, 19 and 28; and in compositions $D_1$ to $D_4$, the compound or compounds of the invention is or are replaced by at least one of compounds Nos. 1, 17 and 27.

This is also the case as regards compositions $E_1$, $E_2$ and $F_1$ and $F_2$.

The following compounds can be incorporated into the compositions indicated below:

Compound 72 into compositions $C_1$ to $C_5$;

Compounds 70, 62 and 60 into compositions $C_1$ to $C_5$ and $F_1$ and $F_2$;

Compound 64 in composition $A_4$;

Compound 64 in the form of the hydrochloride, in compositions $A_1$, $A_3$ and $B_2$; and Compound 57 in compositions $C_2$ and $C_3$

We claim:

1. A compound having the general formula:

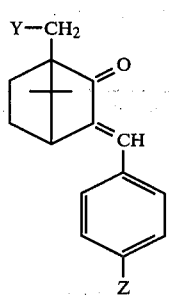

I in which Y denotes hydrogen or the radical $SO_3H$ or a salt thereof with an organic or inorganic base, and Z denotes the radical $-CH_2Br$ or $-CHBrBr$ or a radical $Z'$ which denotes the radical $-CH_2I$, $-CH_2R$, $-CHR'R'$, $-CHO$ or $-COOR''$, in which R denotes $-NR_1R_2$, $-N+R_1R_2R_3$, $-OR_4$, $-OCOR_5$, $-SR_6$, $-CN$, $-COOR''$ or $-SSO3NA$, in which $R_1$ and $R_2$ independently denote hydrogen, $C_{1-18}$ alkyl or hydroxyalkyl, or $R_1$ and $R_2$, together with the nitrogen atom to which they are attached, denote a heterocyclic ring, $R_3$ denotes $C_{1-4}$ alkyl or hydroxyalkyl or sulphonatopropyl, $R_4$ denotes hydrogen, alkyl, polyoxyethylene, aryl which is optionally substituted, menthyl or dialkylaminoalkyl, $R_5$ denotes alkyl, alkenyl, aryl or a 5 or 6 membered heterocyclic ring which is optionally aromatic, and $R_6$ denotes hydrogen, alkyl, carboxyalkyl, aminoalkyl, hydroxyalkyl, aryl or 3-alanyl, $R'$ $R'$ denotes $-OR'_4$ or $-SR'_6$ in which $R'_4$ and $R'_6$ are as defined under $R_4$ and $R_6$, respectively, except for hydrogen, polyoxyethylene, hydroxyalkyl, 3-alanyl and aryl, and $R''$ denotes hydrogen or alkyl, such that when R denotes $N+R_1R_2R_3$, $R_1$ and $R_2$ are not hydrogen and either $R_3$ denotes sulphonatopropyl, or the compound is in the form of a salt with an anion, which is $SO_4$alkyl, $SO_3$aryl, $SO_3$alkyl or halogen or an inorganic or organic acid addition salt thereof when R denotes $-NR_1R_2$ 2. A compound according to claim 1 in which Z denotes $-CH_2Br$ or $-CHBrBr$.

3. A compound according to claim 1 in which Z denotes a radical $Z'$.

4. The compound of claim 1, 3-(4-bromomethylbenzylidene)-camphor.

5. The compound of claim 1, 3-(4-dibromomethylbenzylidene)-camphor.

6. The compound of claim 1, 3-(4-bromomethylbenzylidene)-camphor-10-sulphonic acid.

7. Process for preparing a compound as defined in claim 2 which comprises reacting a compound of the general formula:

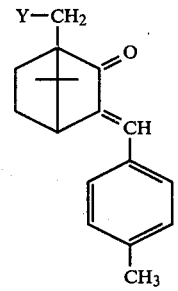

with bromine or with N-bromosuccinimide, in an inert solvent, and in the presence of radiation of wavelength from 200 to 800 nanometres.

8. Process according to claim 7 which is carried out in the presence of a neutralising agent.

9. Process according to claim 7 for preparing a monobrominated compound by using the reactants in stoichiometric amounts.

10. Process according to claim 7 for preparing a dibrominated compound by using the reactants in stoichiometric amounts or with a slight excess of brominating reagent relative to the compound of formula I'.

11. Process for preparing a compound as defined in claim 2, in which Z denotes $-CHBr_2$ which comprises brominating a compound as defined in claim 2 in which Z denotes —CH$_2$Br, the brominating agent being used in stoichiometric amounts or in a slight excess relative to the monobrominated compound.

12. A composition suitable for application to the skin which comprises at least one compound as claimed in any one of claims 1 to 6 and a compatible diluent or carrier.

13. A composition according to claim 12, which contains at least one compound of the formula I or II 0.5 to 10% by weight of the compound, the composition being in the form of a solution, an emulsion, a gel, a dispersion, a suspension or a foam.

14. A composition according to claim 13, which contains 1.5 to 6% by weight of the compound.

15. A composition according to claim 12 which contains at least one cosmetic adjuvant which is lanolin, a fatty acid triglyceride, glycerol, a polyethylene glycol, a oxyethyleneated lanolin, isopropyl myristate or palmitate, castor oil, cetyl/stearyl alcohol, glycerol monostearate, cetyl alcohol, butyl stearate, and organic and inorganic waxes, in an amount from 1 to 40% by weight.

16. A composition according to claim 12 which contains, as a solvent or suspending agent, water, an alcohol, a mixture of alcohols or an aqueous-alcoholic mixture.

17. A composition according to claim 16 in which the solvent or suspending agent is water.

18. A composition according to claim 16 in which the alcohol is ethanol, isopropyl alcohol, propylene glycol, glycerol, sorbitol or oleyl alcohol.

19. A composition according to claim 16 in which the solvent is ethyl alcohol or a mixture of water and ethyl alcohol.

20. A composition according to claim 12 which comprises a solution of oil in alcohol.

21. A composition according to claim 12 in the form of an oil-in-water or water-in-oil emulsion.

22. A composition according to claim 21 which contains at least one compound of formula (I) which is highly soluble in oil, and at least one compound of formula (I) which is highly soluble in water.

23. A composition according to claim 12 which contains at least one compound of formula (I) which is an acid, and at least one compound of formula (I) which is an inorganic or organic salt of the above-mentioned acid.

24. A composition according to claim 12 which contains at least one compound of formula (I) in which Z' denotes the radical —NR$_1$R$_2$, which is at least partially neutralised with an inorganic or organic acid.

25. A composition according to claim 12 which contains an agent for moisturising the skin, in an amount from 0.3 to 3% by weight based on the weight of the composition.

26. A composition according to claim 12 which contains iron oxide in an amount from 0.01 to 0.2% by weight based on the weight of the composition.

27. A composition according to claim 12 which contains a propellant and is packaged in the form of an aerosol container.

28. A composition according to claim 27 in which the propellant is a fluorinated hydrocarbon, carbon dioxide gas, nitrous oxide or a volatile hydrocarbon.

29. A method of bronzing the skin which comprises applying thereto a composition as defined in claim 12.

30. The compound of claim 1, 3-(4-diethylaminomethylbenzylidene)-camphor.

31. The compound of claim 1, 3-(4-diisopropylaminomethylbenzylidene)-camphor.

32. The compound of claim 1, 3-(4-methoxymethylbenzylidence)-camphor.

33. The compound of claim 1, 3-(4-butoxymethylbenzylidene)-camphor.

34. The compound of claim 1, 3-(4-tetradecyloxymethylbenzylidene)-camphor.

35. The compound of claim 1, 3-(4-p-benzoylphenoxymethylbenzylidene)-camphor.

36. The compound of claim 1, 4-(2-oxo-3-bornylidenemethyl)-benzyl tetradecanoate.

37. The compound of claim 1, 4-(2-oxo-3-bornylidenemethyl)-benzoic acid.

38. The compound of claim 1, 3-(4-dimethylaminoethoxymethylbenzylidene)-camphor.

39. The compound of claim 1, 3-[4-(2-oxo-3-bornylidenemethyl-benzylthio]-propionic acid.

40. The compound of claim 1, N-(2-hydroxyethyl)-N-[4-(2-oxo-3-bornylidenemethyl)-benzyl]-dimethylammonium bromide.

41. The compound of claim 1, 3-(4-oleyloxymethylbenzylidene)-camphor.

42. The compound of claim 1, N,N'-bis-(2-hydroxyethyl)-N-[4-(2-oxo-3-bornylidenemethyl)-benzyl]-piperazinium bromide.

43. The compound of claim 1, wherein Z is either —CH$_2$Br or —CHBr$_2$.

44. The compound of claim 1, wherein Z' is —CH$_2$I.

45. The compound of claim 1, wherein R is —NR$_1$R$_2$.

46. The compound of claim 1, wherein Z' is —CH$_2$-NR$_1$R$_2$R$_3$.

47. The compound of claim 1, wherein R is —OR$_4$; —SR$_6$; or —OCOR$_5$.

48. The compound of claim 1, wherein Z' is —CHR'R'.

49. The compound of claim 1, wherein Z' is —CHO.

50. The compound of claim 1, wherein Z' is —COOR".

51. The compound of claim 1, wherein R is —CN.

* * * * *